United States Patent [19]

Takeda et al.

[11] Patent Number: 4,957,363
[45] Date of Patent: Sep. 18, 1990

[54] APPARATUS FOR MEASURING CHARACTERISITCS OF PARTICLES IN FLUID BY DETECTING LIGHT SCATTERED AT THE PARTICLES

[75] Inventors: Kazuo Takeda, Kokubunji; Yoshitoshi Ito, Ome, both of Japan

[73] Assignee: Hitachi, Ltd., Tokyo, Japan

[21] Appl. No.: 214,515

[22] Filed: Jul. 1, 1988

[30] Foreign Application Priority Data

Jul. 3, 1987 [JP] Japan .................... 62-165176

[51] Int. Cl.⁵ .................. G01N 15/14; G01N 21/53
[52] U.S. Cl. ....................... 356/73; 250/222.2; 356/336; 356/343
[58] Field of Search .......... 356/73, 336, 338, 339, 356/343, 72; 250/222.2

[56] References Cited

U.S. PATENT DOCUMENTS

| | | | |
|---|---|---|---|
| 3,835,315 | 9/1974 | Gravitt, Jr. ........... | 250/225 X |
| 3,851,169 | 11/1974 | Faxvog ............... | 250/222.2 |
| 4,348,111 | 9/1982 | Goulas et al. ......... | 356/336 |
| 4,352,558 | 10/1982 | Eisert ................ | 356/73 X |
| 4,573,796 | 3/1986 | Martin et al. ......... | 356/73 X |
| 4,636,075 | 1/1987 | Knollenberg .......... | 356/338 X |
| 4,667,830 | 5/1987 | Nozaki, Jr. et al. .... | 356/72 X |

FOREIGN PATENT DOCUMENTS 54-114260 2/1978 Japan .

*Primary Examiner*—Vincent P. McGraw
*Attorney, Agent, or Firm*—Antonelli, Terry, Stout & Kraus

[57] ABSTRACT

In a particle measuring apparatus for measuring characterisitcs of particles by detecting light scattered at the particles while irradiating the particles in fluid with light, the scattered light is detected by means of a plurality of detectors and the characterisitcs of particles are determined by using pulse signals of detection signals coming from the plurality of detectors, which are coincident with each other.

5 Claims, 4 Drawing Sheets ately. The gate circuits 15 and 16 open the gates, only when the gate signal is produced by the gate signal pulse generator 14; 17 and 18 are A/D converters transforming analogue signals outputted by the gate circuits 15 and 16 into digital signals; and 19 is an IC memory for storing signals outputted by the A/D converters 17 and 18.

APPARATUS FOR MEASURING CHARACTERISITCS OF PARTICLES IN FLUID BY DETECTING LIGHT SCATTERED AT THE PARTICLES

BACKGROUND OF THE INVENTION

This invention relates to a particle measuring system for measuring characteristics of particles such as number, size, refractive index, shape, etc. by detecting light scattered at the particles by means of detectors while irradiating the particles in fluid such as liquid with light.

In a prior art particle measuring apparatus, as described in JP No. A-54-114260, pulse signals for measuring characteristics of particles are detected by using signals coming from a detector.

However, when pulse signals for measuring characteristics of particles are detected by using signals coming from a detector as in the prior art particle measuring apparatus, since noises are produced in the detector, etc., it is not possible to measure particles generating scattered light pulses, which are smaller than those due to these noises, i.e. particles, whose size is small.

SUMMARY OF THE INVENTION

This invention has for its object to provide a particle measuring apparatus, by means of which it is possible to measure particles, whose size is small.

In order to achieve the above object, according to one aspect of this invention, in a particle measuring apparatus for measuring characteristics of particles by detecting light scattered at the particles while irradiating the particles in fluid with light, the scattered light is detected by means of a plurality of detectors and the characteristics of particles are determined by using pulse signals of detection signals coming from the plurality of detectors, which are coincident with each other.

In this particle measuring apparatus, the characteristics of particles are determined by using pulse signals of detection signals coming from the plurality of detectors, which are coincident with each other, because, even if noises are produced in the detectors, etc., noise pulses are removed and therefore it is possible to measure characteristics of particles by using only pulses due to light scattered at the particles.

DESCRIPTION OF THE PREFERRED EMBODIMENTS

Figure 1:
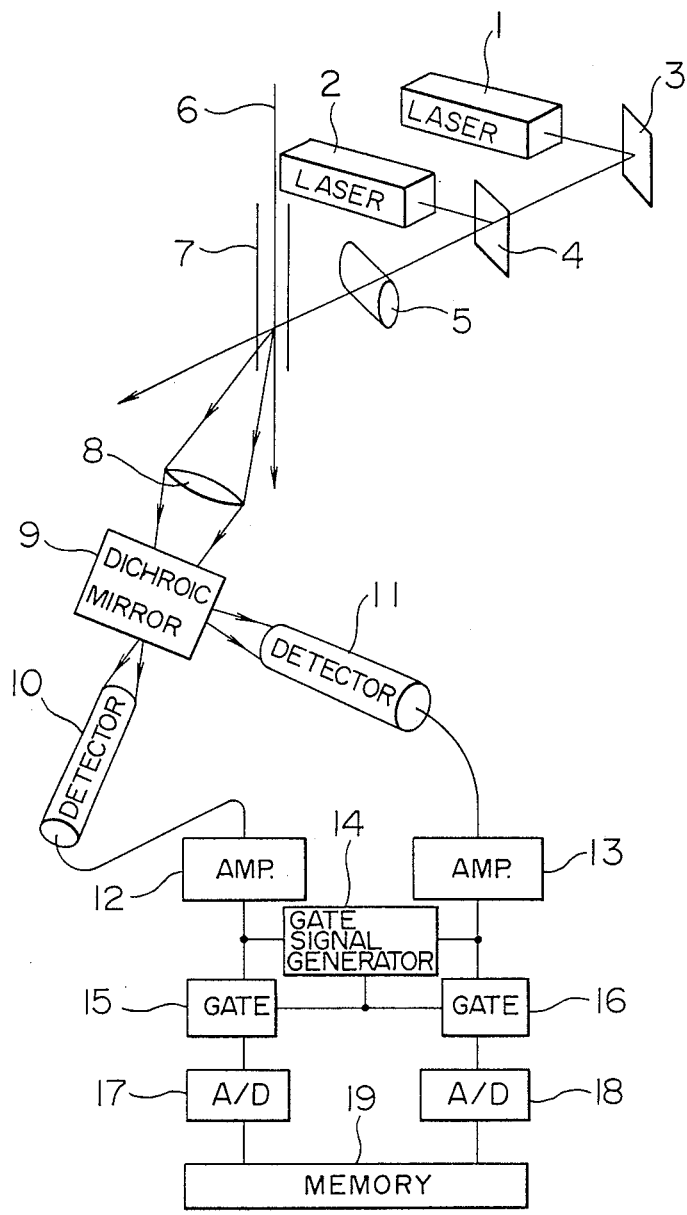
FIG. 1 is a scheme illustrating a particle measuring apparatus according to this invention.

FIG. 1 is a scheme illustrating a particle measuring apparatus according to this invention; In the figure, reference numeral 7 is a flow cell made of glass; 6 is suspension of sample particles in water flowing through the flow cell 7; 1 is a He-Cd laser light source; 2 is a He-Ne laser light source, the wavelength of the laser light emitted by the laser light source 2 being different from that emitted by the laser light source 1; 3 is a mirror reflecting the laser light emitted by the laser light sources 1; 4 is a dichroic mirror transmitting the light reflected by the mirror 3 and reflecting the laser light emitted by the laser light source 2; 5 is a focusing lens focusing the laser light and irradiating the suspension 6 of sample particles therewith; 9 is a dichroic mirror separating scattered light produced by particles in the suspension 6 of sample particles in wavelength; 8 is a focusing lens for focusing the scattered light on the dichroic mirror 9; 10 and 11 are detectors for detecting the scattered light separated by the dichroic mirror 9 in wavelength; 12 and 13 are amplifiers for amplifying signals detected by the detectors 10 and 11, respectively; 14 is a gate signal pulse generator for generating a gate signal pulse, when the pulse of the signal detected by the detector 10 and that detected by the detector 11 are coincident; 15 and 16 are gate circuits opening the gates, only when the gate signal is produced by the gate signal pulse generator 14; 17 and 18 are A/D converters transforming analogue signals outputted by the gate circuits 15 and 16 into digital signals; and 19 is an IC memory for storing signals outputted by the A/D converters 17 and 18.

Figure 2:
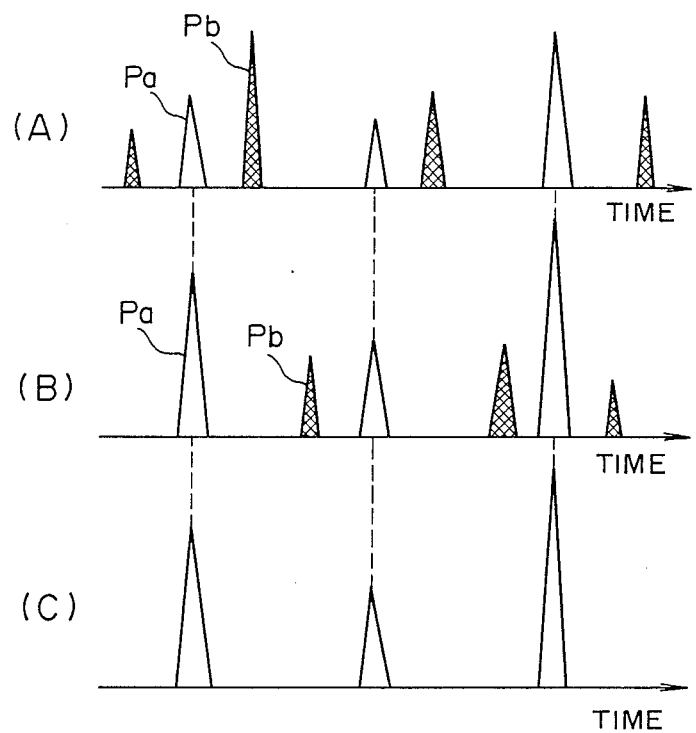
FIG. 2 indicates output signals of an amplifier, another amplifier and a gate circuit of the particle measurement apparatus indicated in FIG. 1.

In this particle measuring apparatus, when the laser light sources 1 and 2 emit laser light in the state that the suspension 6 of sample particles flows through the flow cell 7, the suspension 6 of sample particles is irradiated with the laser light and scattered light is produced at the moment where a particle in the suspension 6 of sample particles traverses the laser light beam. This scattered light is collected on the dichroic mirror 9 by the focusing lens 8 and the scattered light is separated in wavelength by the dichroic mirror 9. The scattered light separated in wavelength is detected by the detectors 10 and 11 and the output signals of the detectors 10 and 11 are amplified by the amplifiers 12 and 13, respectively. The gate signal generator 14 generates a gate signal pulse, when the pulse of the signal detected by the detector 10 and that detected by the detector 11 are coincident with each other. The gate circuits 15 and 16 open the gates, only when the gate signal is produced by the gate signal generator 14. The A/D converters 17 and 18 transform analogue signals of the gate circuits 15 and 16 into digital signals, respectively, and the IC memory stores the output signals of the A/D converters 17 and 18. For example, the amplifier 12 outputs a signal as indicated in FIG. 2(A). When the amplifier 13 outputs a signal as indicated in FIG. 2(B), the gate circuit 16 outputs a signal as indicated in FIG. 2(C). That is, in the output signals of the amplifiers 12 and 13 there exist mixedly pulses $P_a$ due to the scattered light and noise pulses $P_b$. However, since the scattered light produced by one particle is detected simultaneously by the detectors 10 and 11, the timings of the detection of a pulse $P_a$ by them are coincident. On the contrary, since the timings of the detection of pulses $P_b$ are not coincident, if the gate circuits 15 and 16 are opened only when the timings of the detection of pulses are coincident, the pulses $P_b$ whose detections are not coincident are removed and the signals outputted by the gate circuits 15 and 16 contain only pulses $P_a$ due to the scattered light. Consequently, even if noise pulses $P_b$ arise in the output signals of the amplifiers 12 and 13, it is possible to measure characteristics such as number, size, refractive index of the particles by using only the pulses $P_a$ due to the scattered light coming from the particles.

Figure 3:
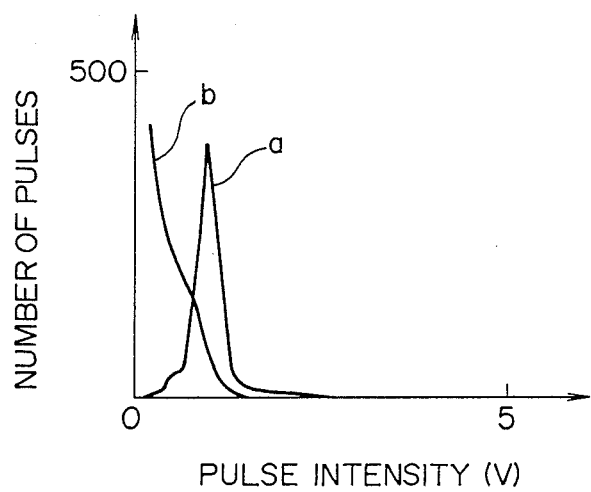
FIG. 3 is a graph indicating a distribution of only pulses due to light scattered at particles and a distribution of noise pulses.

FIG. 3 is a graph (data for a wavelength of 632.8 nm) illustrating the relationship between the pulse intensity and the number of pulses, in the case where a suspension of sample polystyrene particles having a size of 1.1 μm in water is made to flow through the flow cell, which is irradiated with laser lights having wavelengths of 441.6 nm and 632.8 nm, and light forward scattered by particles is separated in wavelength by means of the monochrometer, separated scattered lights being detected separately by means of different detectors. The curve a indicates the distribution of pulses, for which the detection signals of the two detectors are coincident, i.e. the distribution of pulses produced exclusively by light scattered by particles and the curve b indicates the distribution of pulses, for which the detection signals of the two detectors are not coincident, i.e. the distribution of only noise pulses. As clearly seen from this graph, since the curves a and b intersect each other, by means of a prior art particle measuring apparatus it is impossible to measure particles, for which the pulse intensity is low, i.e. whose size is small. On the contrary, by means of a particle measuring apparatus according to this invention, it is possible to measure particles whose size is small. In addition, starting from pulse intensity distributions obtained for different wavelengths, it is possible also to obtain the size and the refractive index of the particles.

Figure 4:
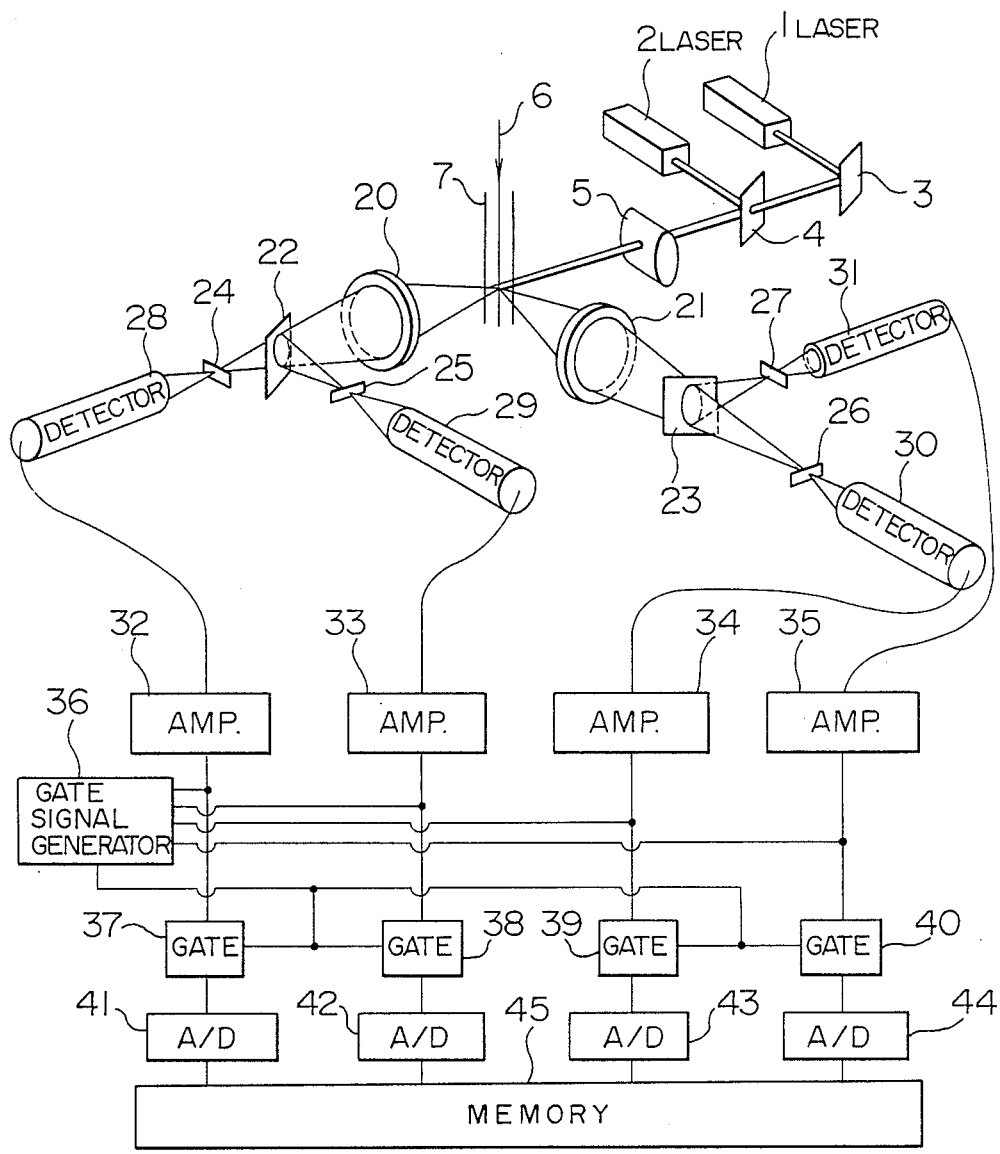
FIG. 4 is a scheme illustrating another particle measuring apparatus according to this invention.

FIG. 4 is a scheme illustrating another particle measuring apparatus according to this invention. In the figure reference numerals 22 and 23 are dichroic mirrors separating scattered light produced by particles in the suspension 6 of sample particles in wavelength; 24 to 27 are slits for removing stray light in the scattered light transmitted by the dichroic mirrors; 20 and 21 are focusing lenses collecting the scattered light on the slits 24 to 27; 28 to 31 are detectors detecting the scattered light separated by the dichroic mirrors in wavelength; 32 to 35 are amplifiers amplifying detection signals from the detectors 28 to 31, respectively; 36 is a gate signal generator, in which output signals of the amplifiers 32 to 35 are inputted and which generates a gate signal pulse, when pulses of detection signals from the detectors 28 to 31 are coincident; 37 to 40 are gate circuits opening the gates, only when the gate signal is produced by the gate signal generator 36; 41 to 44 are A/D converters transforming analogue signals outputted by the gate circuits 37 to 40 into digital signals; and 45 is an IC memory storing output signals of the A/D converters 41 to 44.

In this particle measuring apparatus, since the gate circuits 37 to 40 are opened only when the pulses of the detection signals outputted by the detectors 28 to 31 are coincident, pulses which are not coincident are removed and therefore the output signals from the gate circuits 37 to 40 are constituted only by pulses due to the scattered light. Consequently, even if noise pulses arise in the output signals from the amplifiers 32 to 35, it is possible to measure characteristics of particles by using exclusively pulses due to the light scattered by the particles.

In particular, according to this embodiment, since four detectors are used, it is possible to obtain the size and the refractive index of the particles with a higher precision.

Figure 5:
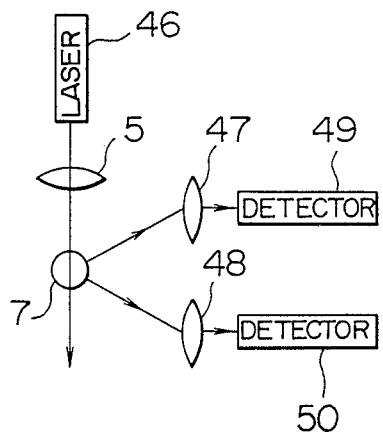
FIGS. 5 to 7 are schemes illustrating partially other different particle measuring apparatuses according to this invention.

FIG. 5 is a scheme illustrating a part of still another particle measuring apparatus according to this invention. In the figure reference numeral 46 is a He-Cd laser light source; 49 and 50 are detectors detecting scattered light produced by particles in the suspension 6 of sample particles; and 47 and 48 are focusing lenses collecting the scattered light on the detectors 49 and 50, respectively. Amplifiers, a gate signal generator, gate circuits, A/D converters and an IC memory are connected with the detectors 49 and 50, just as in the particle measuring apparatus indicated in FIG. 1.

In this particle measuring apparatus, since characteristics of the particles are measured by using pulses of the detection signals coming from the detectors 49 and 50, which are coincident, it is possible to measure the characteristics, i.e. number, approximate size, etc. of the particles by using exclusively pulses due to the light scattered by the particles.

Figure 6:
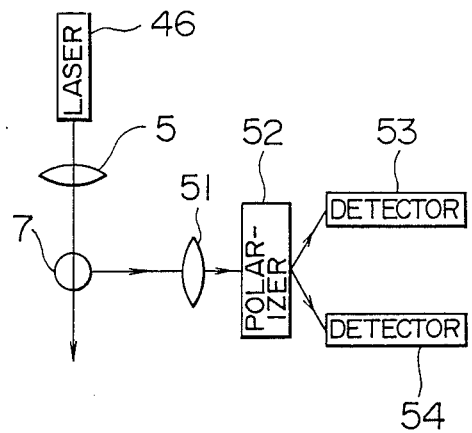

FIG. 6 is a scheme illustrating a part of still another particle measuring apparatus according to this invention. In the figure reference numeral 52 is a polarizer dividing scattered light into different polarization components; 51 is a focusing lens collecting the scatted light produced by the particles in the suspension 6 of sample particles on the polarizer 52; and 53 and 54 are detectors detecting the scattered light divided by the polarizers 53 and 54. Amplifiers, a gate signal generator, gate circuits, A/D converters and an IC memory are connected with the detectors 53 and 54, just as in the particle measuring apparatus indicated in FIG. 1.

In this particle measuring apparatus, since characteristics of the particles are measured by using pulses of the detection signals coming from the detectors 53 and 54, which are coincident, it is possible to measure the characteristics, i.e. number, approximate size, shape, etc. of the particles by using exclusively pulses due to the light scattered by the particles.

Figure 7:
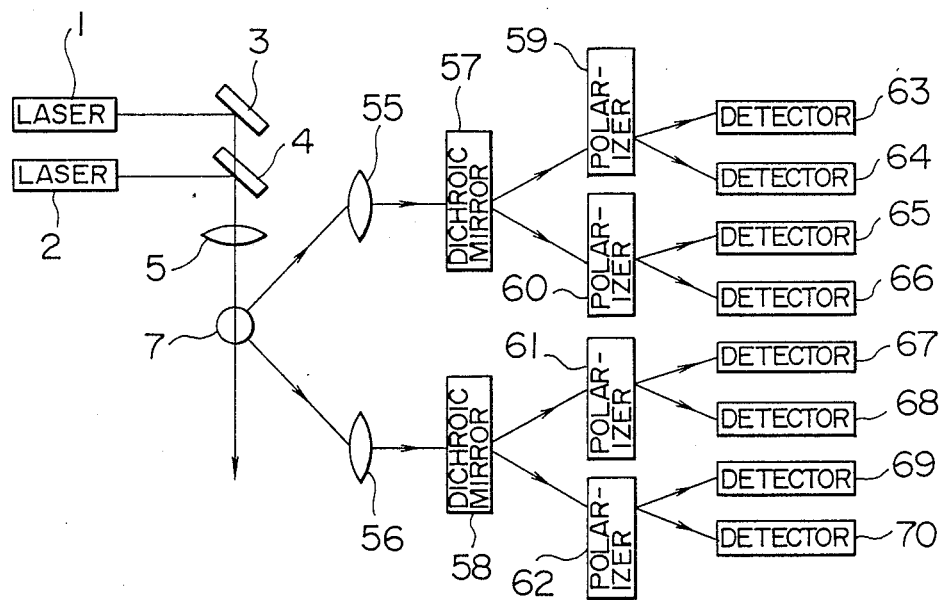

FIG. 7 is a scheme illustrating a part of still another particle measuring apparatus according to this invention. In this figure reference numerals 57 and 58 are dichroic mirrors separating scattered light produced by particles in the suspension 6 of sample particles in wavelength; 55 and 56 are focusing lenses collecting the scattered light on the dichroic mirrors 57 and 58; 59 to 62 are polarizers dividing the scattered light separated by the dichroic mirrors 57 and 58 in wavelength into different polarization components; and 63 to 70 are detectors detecting the scattered light divided by the polarizers 59 to 62, respectively. Amplifiers, a gate signal generator, gate circuits, A/D converters and an IC memory are connected with the detectors 63 to 70. The output signals from the detectors 63 to 70 are amplified by the amplifiers. The gate signal generator generates a gate signal pulse, only when pulses of the detection signals from the detectors 63 to 70 are coincident and the gate circuits open the gates, only when the gate signal from the gate signal generator arises. The A/D converters transform analogue signals outputted by the gate circuits into digital signals and the IC memory stores the signals outputted by the A/D converters.

On the other hand a table is previously prepared by a numerical analysis using a light scattering theory (Mie, Ann, Phys. 25 (1908) 377 or Asano & Yamamoto, Appl. Opt. 14 (1975) 29), concerning values of the size, the refractive index and the shape (aspect ratio) of the particles corrresponding to scattering intensities. In this way it is possible to obtain a set of values of the size, the refractive index and the shape, starting from a set of scattering intensities obtained by measurements.

In this particle measuring apparatus, since characteristics of the particles are measured by using pulses of the detection signals coming from the detectors 63 to 70, which are coincident, it is possible to measure the characteristics of the particles by using exclusively pulses due to the light scattered by the particles.

In particular, in this embodiment, since two laser light beams having different wavelengths, four polarizers and eight detectors are used, it is possible to obtain the size, the refractive index and the shape of the particles with a higher precision.

Furthermore, although, in the embodiment described above, explanation has been made on measurements of particles suspended in water 6, this invention can be applied as well to measurements of particles suspended in other fluids.

As explained above, by means of the particle measuring apparatus according to this invention, even if noises are produced by detectors, etc., since characteristics of particles are measured by using exclusively pulses due to light scattered by the particles, it is possible to measure also particles having a small size with a high precision.

We claim:

1. A particle measurement apparatus comprising:
   means for generating laser lights having wavelengths which are different from each other;
   a flow cell through which a fluid sample including particles flows;
   focusing means for collecting said laser lights and for irradiating said fluid sample therewith;
   monochrometer means for wavelength-separating scattered light from said particles;
   a plurality of detector means for detecting the wavelength-separated scattered light from said monochrometer means; and
   measuring means for extracting output pulse signals of said plurality of detector means which are indicative of said particles and which are coincident with each other in timing of detection so as to enable measurement of the number, size and refractive index of said particles by use of said extracted output pulse signals of said plurality of detector means.

2. A particle measurement apparatus according to claim 1, wherein said monochrometer means includes a plurality of monochrometers.

3. A particle measurement apparatus according to claim 1, wherein said measuring means includes a memory for storing said extracted output pulse signals.

4. A particle measurement apparatus comprising:
   means for generating laser lights having wavelengths which are different from each other;
   a flow cell through which a fluid sample including particles flows;
   focusing means for collected said laser lights and for irradiating said fluid sample therewith;
   a plurality of monochrometer means each of which wavelength-separates scattered light from said particles;
   a plurality of polarization dividing means associated with said plurality of monochrometer means for receiving the wavelength separated scattered light from the associated monochrometer means so that said plurality of polarization dividing means divides the received wavelength-separated scattered light into different polarized components;
   a plurality of detector means for detecting the different polarized components from said plurality of polarization dividing means; and
   measuring means for extracting output pulse signals of said plurality of detector means which are indicative of said particles and which are coincident with each other in timing of detection so as to enable measurement of characteristics of said particles.

5. A particle measurement apparatus according to claim 4, wherein each of said plurality of polarization dividing means includes a plurality of polarizers for the associated monochrometer means, each of said plurality of polarizers dividing the wavelength-separated scattered light from the associated monochrometer means into different polarized components.

* * * * *